United States Patent [19]

Krul

[11] Patent Number: 4,931,394
[45] Date of Patent: Jun. 5, 1990

[54] VITRO PROPAGATION OF GRAPE VIA LEAF DISK CULTURE

[75] Inventor: William R. Krul, Narragansett, R.I.

[73] Assignee: The Board of Governors for Higher Education, State of Rhode Island and Providence Plantations, Providence, R.I.

[21] Appl. No.: 265,215

[22] Filed: Oct. 31, 1988

Related U.S. Application Data

[63] Continuation of Ser. No. 24,036, Mar. 10, 1987.

[51] Int. Cl.$^5$ .............................................. C12N 5/00
[52] U.S. Cl. .................................. 435/240.45; 47/58; 435/240.49; 435/240.51
[58] Field of Search ............ 47/58; 435/240.4, 240.45, 435/240.46, 240.47, 240.48, 240.49, 240.5, 240.51, 240.54

[56] References Cited

PUBLICATIONS

Evans et al., (1981) in Plant Tissue Culture, Methods and Application in Agriculture, TA Thorpe, ed, Academic Press, NY, pp. 45-113.
F. Constabel (1984) in Cell Culture and Somatic Cell Genetics of Plants, vol. 1, IK Vasel, ed, Academic Press, NY, p. 28.
Amita Pol et al., (1985), Plant Cell Reports, 4:281-284.

Primary Examiner—Charles F. Warren
Assistant Examiner—Charles E. Cohen
Attorney, Agent, or Firm—Samuels, Gauthier & Stevens

[57] ABSTRACT

Angiosperm nodes are cultured to develop plantlets. The plantlets are exposed to photoperiods of light and dark. Leaf tissue removed from the plantlets when cultured produces at least 20% embryos.

6 Claims, 1 Drawing Sheet

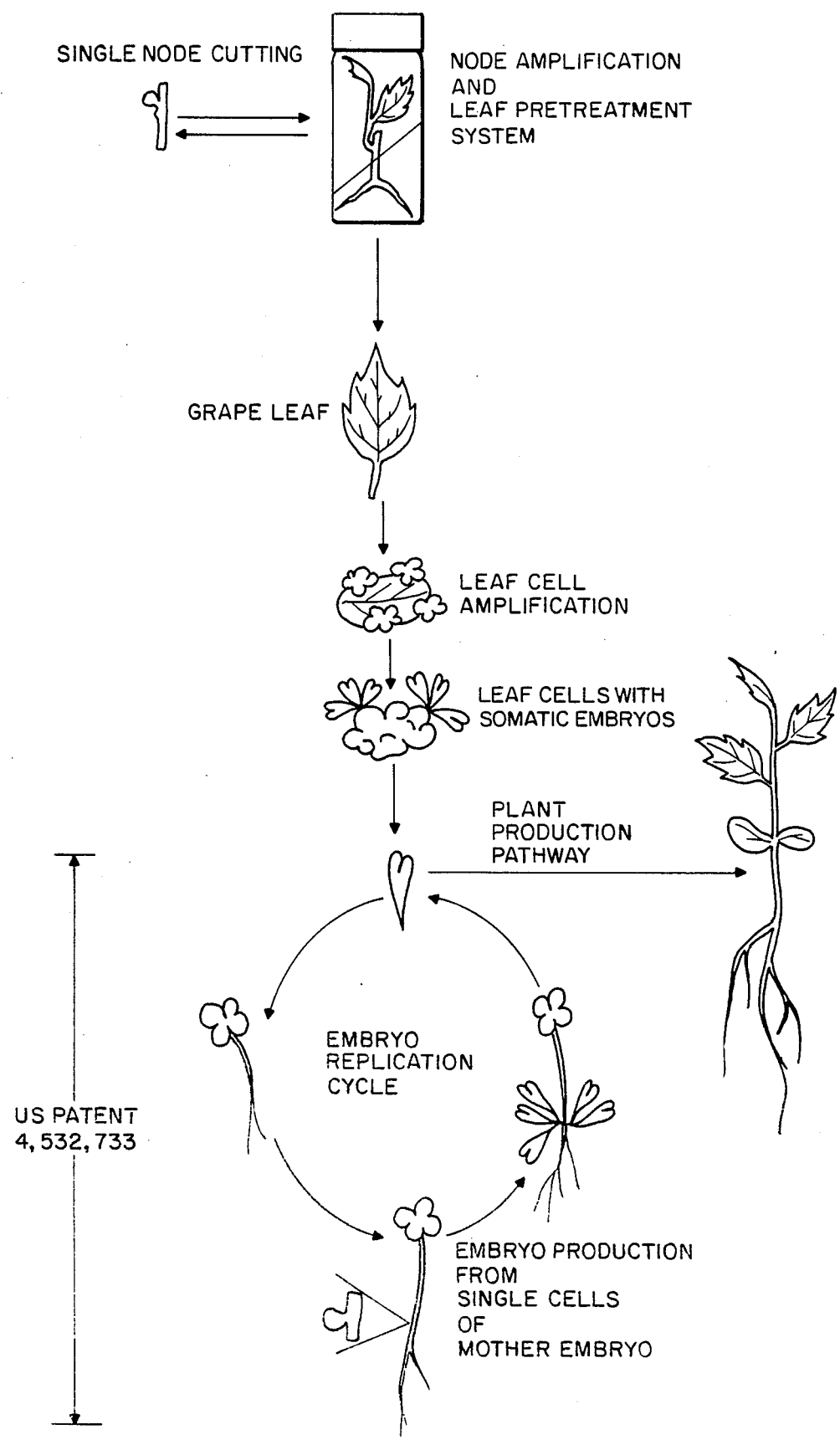

VITRO PROPAGATION OF GRAPE VIA LEAF DISK CULTURE

This is a continuation of co-pending application Ser. No. 024,036 filed on 03/10/87.

BRIEF SUMMARY OF THE INVENTION

The invention is directed to a method of producing somatic embryos from tissue culture and the embryos and plants produced from said method.

Irrespective of the plant species, there are a number of common features that apply to most tissue culture programs. The techniques of cell and tissue culture have been widely developed and much work has been done on the growth, metabolism and differentiation of tissue culture of dicotyledons (Yamada, 1977 in plant cell, tissue and organ culture, Reinert and Bagjaj (eds.), pp. 144–159, Springer-Verlag, Berlin). In Maize, the development of tissue cultures capable of plant regeneration is also known (Green and Rhodes, 1982 Maize for Biological Research, W. F. Sheridan (ed.), pp. 367–371, Plant Molecular Biology Association, Charlottsvile, Va.) and U.S. Pat. No. 4,581,847. The development of somatic embryos from tissue culture with angiosperms is also known Wetherell, D. W. 1978, In vitro Embryoid Formation in Cells Derived from Somatic Plant Tissues and in Propagation of Higher Plants Through Tissue Culture—A Bridge Between research and Application. Eds. K. W. Hughes, R. Henke, M. Constatin. Published by Technical Information Center US Dept. Energy, Conf-7804111.

The development of tissue cultures capable of plant regeneration can usually be accomplished after identification of the appropriate genotypes and donor tissues. Success is frequently dependent upon choosing donor tissues for culture initiation which come from plants of appropriate genotype as well as physiological and development states. Other features which are also important include the organic and inorganic composition of the growth medium and the physical environment in which the cultures are grown.

My invention is directed to a method for the production of somatic embryos and the embryos produced by the method and the plants produced from said embryos. The embryos produced by the method disclosed herein may advantageously be used as the somatic embryos in the method disclosed in my U.S. Pat. No. 4,532,733.

My method has utility for the rapid clonal multiplication of new plants from somatic cells, it provides a method for the selection of induced or spontaneous mutant plants, for the production and selection of plants that are altered by insertion of foreign genes by appropriate gene vectors and for the multiplication of altered plants in accordance with the teachings of this disclosure.

In the preferred embodiment, a method for the clonal propagation of certain angiosperms, a definitive listing and identification of these members of the genera is set forth in Murashige, T. 1978. The Impact of Plant Tissue Culture on Agriculture. In: Frontiers of Plant Tissue Culture 1978. Editor: T. A. Thorpe. Publisher: The International Association for Plant Tissue Culture. Distributed by: The Bookstore, University of Calgary, Alberta T2N 1N4, Canada which publication is hereby incorporated by reference in its entirety in this disclosure, and particularly, the Vitis species hybrid cultivar "Seyval" is described. It is believed that my method is equally applicable to most biennial and perennial angiosperms, especially to the families Vitaceae and Rhamnaceae and to members of the class Coniferales, with perennial growth habits.

This method can be used to produce somatic embryos from plant cells and in the preferred embodiment the embryos are produced from leaf cell cultures. The mother plants from which leaf tissue (cells) is taken are cultured under controlled conditions of light and darkness and growth supplements. Prior art processes for the production of somatic embryos from leaf tissue is a relatively rare event e.g. one tissue culture isolate in one hundred may produce somatic embryos. In the method described herein 100% of the tissue culture isolates produced somatic embryos.

BRIEF DESCRIPTIONS OF THE DRAWING

The drawing is a schematic view of the method of the invention.

DESCRIPTION OF THE PREFERRED EMBODIMENT(S)

The method involves isolation of leaf disk segments (isolates) from grapevines (mother plants) that are grown in a specific physical environment and treated with plant growth regulators in specific amounts and in the appropriate sequence. The isolates from such mother plants are then grown on traditional cell culture medium and embryos regenerated by established procedures.

EXAMPLE

The experimental protocol for detection of the appropriate pretreatment of the mother plants was as follows: Seyval plants, originally derived from somatic embryos, were maintained by culture of isolated single nodes in culture tubes on hormone free, ½ strength M&S (1962) medium under ambient temperature and pressure with photoperiods of 16h light and 8h dark. The cuttings (plantlets) were illuminated with cool white fluorescent lamps ($40\mu e/m^2/s^2$).

Single node cuttings (green wood) from plants grown in the field may also provide starting materials. However, such cuttings require the development of juvenile characteristics prior to treatment for embryo induction. Juvenility can be induced by passage of nodal cuttings through one or more in vitro cultures on M&S medium without growth regulators. Cuttings of field grown plants from some species may require low concentrations of an auxin, to stimulate root initiation, prior to induction of juvenile growth. Once juvenile characters have been developed then subsequent propagation by node cutting can be carried out on hormone free M&S medium.

After 14 days various concentrations of (see the Table) of either or both 6-benzylamino purine (BA) or gibberellic acid A3 (GA) were supplied to these cultured plantlets. In cases where both growth regulators were applied one would precede the other by one week.

Seven days after the last growth regulator application (14 days if only one applied), one group of plantlets remained under the photoperiod conditions above, namely 16h light and 8h dark. Another group of plantlets was cultured under a photoperiod of 8h light and 16h dark. Still another group of plantlets were cultured under continuous illumination. Illumination was also 40 $\mu e/m^2/s$ for the latter two groups.

The plantlets were removed from the culture tubes and all leaves that had attained or were close to full expansion were excised with a scalpel and cut into segments (leaf tissue) of approximately 100mm². Each segment contained a portion of the main vein.

The leaf tissue was cultured on M&S medium supplemented with 2mg/l 2,4-dichlorpheoxyacetic acid and 1 mg/l 6-benzylaminopurine and such cultures were maintained in the dark for three weeks. Cultures grown in the light did not produce embryos even with favorable pretreatment. After three weeks the callus that developed was transferred to a medium of M&S salts supplemented with 1 mg/l of anapthaleneacetic acid and embryo production was scored after 15 days.

The specific treatments and the results were:

TABLE

| Pretreatment (mg/l) | Embryos Produced (% isolates) |
| --- | --- |
| Light Condition 16h-light-8h-dark | |
| control | 0 |
| 0.001 BA | 40 |
| 0.001 GA | 0 |
| 0.01 BA | 0 |
| 0.01 GA | 20 |
| 0.1 BA | 20 |
| 0.1 GA | 0 |
| 1.0 BA | 20 |
| 1.0 GA | 50 |
| control | 0 |
| 0.001 BA + 0.001 GA | 0 |
| 0.001 GA + 0.001 BA | 40 |
| 0.01 BA + 0.01 GA | 60 |
| 0.01 GA + 0.01 BA | 20 |
| 0.1 BA + 0.1 GA | 0 |
| 0.1 GA + 0.1 BA | 20 |
| 1.0 BA + 1.0 GA | 40 |
| 1.0 GA + 1.0 BA | 0 |
| Light Condition 8h-light-16h dark | |
| Control | 0 |
| 0.001 BA + 0.001 GA | 100 |
| 0.001 GA + 0.001 BA | 0 |
| 0.01 BA + 0.01 GA | 0 |
| 0.01 GA + 0.01 BA | 0 |
| 0.1 BA + 0.1 GA | 0 |
| 0.1 GA + 0.1 BA | 0 |
| 1.0 BA + 1.0 GA | 0 |
| 1.0 GA + 1.0 BA | 0 |
| Continuous light | |
| control | 0 |
| 0.001 BA + 0.001 GA | 0 |
| 0.001 GA + 0.001 BA | 0 |
| 0.01 BA + 0.1 GA | 0 |
| 0.01 GA + 0.1 BA | 0 |
| 0.1 BA + 0.1 GA | 0 |
| 0.1 GA + 0.1 BA | 0 |
| 1.0 BA + 1.0 GA | 0 |
| 1.0 GA + 1.0 BA | 0 |

The data shows that none of the control treatments produced somatic embryos from the leaf disks when cultured by standard embryo induction procedures. However, the light conditions and plant growth regulator pretreatment significantly and unexpectedly enhanced the production of somatic embryos from the isolates. The most efficient treatment for embryo initiation was mother plant culture with 8h-light-16h dark with 7 days exposure to 0.001 mg BA followed by 7 days exposure to 0.001 mg GA. This treatment resulted in embryo production by 100% of the leaf disk isolates.

Pretreatment of in vitro cultured plants that display juvenile characteristics such as loss of tendril or thorn production, alteration of leaf arrangement (phyllotaxy) and/or transition of leaf morphology to the seedling state (generally simple entire leaves with reduction in intensity and quantity of lobe formation and a reduction in hair cell production) with both photoperiod and subsequent exposure to either or both a cytokinin or gibberelin will precondition such "mother tissues" to display more efficient production of somatic embryos when isolates made from them are cultured on standard embryo induction medium.

Other plant growth regulators suitable for the invention include: isopentenyladenine, zeatin, kinetin, and other substituted adenine compounds, phenylureas that display cytokinin activity, auxins as indole-3-acetic acid, indolebutryic acid, naphthoxyacetic acid, 2,4,5,-trichlorophenoxyacetic acid, 4-chloprophenoxyacetic acid, 2,4-dimethylphenoxyacetic acid and 4-amino-3,5,6 trichloropicolinic acid.

The specific treatments set forth above are, of course, exemplary. The specific number of days may vary and the alternating periods may be uniform or non-uniform. That is, it is believed with either the Seyval plants or others described herein that six days followed by six days or eight days followed by eight days (uniform) or six days followed by eight or eight days followed by six or seven days followed by six, etc. (non-uniform) would be equally successful. Similarly, the photoperiods of sixteen hours light and eight hours dark or eight hours light and sixteen hours dark may vary to be other than multipliers of two. That is, it could be seven hours followed by seventeen or nine followed fifteen or other combinations of time periods could be used. As should be readily apparent, the development characteristics in the various stages determines when one stage has finished and the next stage commences.

Lastly, the concentrations of growth regulators added will vary depending upon plants being processed and the process paramters selected. Again, visual observation of the development in each stage will determine the optimum processing conditions.

Having described my invention, what I now claim is:
I claim:

1. A method for producing somatic embryos which includes:
    (a) isolating single nodes selected from plants of the cultivar Seyval;
    (b) culturing said nodes to develop plantlets;
    (c) culturing said plantlets by: exposing the plantlets to alternating photoperiods of light and dark; and adding effective amounts of growth regulators selected from the group consisting of 6-benzylaminopurine and gibberellic acid A3 to said plantlets during the exposure periods of step (c);
    (d) exposing subsequently the plantlets of step (c) to alternate photoperiods of light and dark; and
    (e) removing leaf tissue including a portion of the main vein, from the plantlets of step (d) and culturing the same, at least 20% of said leaf tissues producing embryos.

2. The method of claim 1 wherein the growth regulator is 6-benzylaminopurine.

3. The method of claim 1 wherein the growth regulator is gibberellic acid A3.

4. The method of claim 1 wherein the growth regulators comprise a combination of 6-benzylaminopurine and gibberellic acid A3.

5. The method of claim 1 which includes: exposing the plantlets of step C first to a photoperiod of dark and subsequently to a photoperiod of light.

6. The method of claim 1 which includes culturing the leaf tissue in the dark.

* * * * *